United States Patent [19]

Goetz et al.

[11] 4,298,733

[45] Nov. 3, 1981

[54] PREPARATION OF CIS-2,6-DIMETHYLMORPHOLINE

[75] Inventors: Norbert Goetz, Worms; Walter Himmele, Walldorf; Leopold Hupfer, Friedelsheim, all of Fed. Rep. of Germany

[73] Assignee: BASF Aktiengesellschaft, Fed. Rep. of Germany

[21] Appl. No.: 184,816

[22] Filed: Sep. 8, 1980

[30] Foreign Application Priority Data

Sep. 25, 1979 [DE] Fed. Rep. of Germany ....... 2938698

[51] Int. Cl.$^3$ ........................................... C07D 265/30
[52] U.S. Cl. ................................................. 544/106
[58] Field of Search ........................................ 544/106

[56] References Cited

U.S. PATENT DOCUMENTS 3,083,202  3/1963  Summers ............................ 544/106
4,212,972  7/1980  Goetz et al. ........................ 544/106

OTHER PUBLICATIONS

Houben-Weyl, *Met. der Org. Chemie*, vol. 4/2 pp. 227–283.
Zelinsky et al., *Br. dtsch. Chem. Ges.*, vol. 65 (1932) pp. 1613–1617.

*Primary Examiner*—Henry R. Jiles
*Assistant Examiner*—R. W. Ramsuer
*Attorney, Agent, or Firm*—Keil & Witherspoon

[57] ABSTRACT

A process for the preparation of cis-2,6-dimethylmorpholine by isomerizing trans-2,6-dimethylmorpholine, wherein trans-2,6-dimethylmorpholine is converted, in the presence of hydrogen and of a catalyst containing palladium as well as zinc, cadmium or manganese or a mixture of these, at from 150° to 250° C. under a pressure of from 1 to 200 bar.

2 Claims, No Drawings

PREPARATION OF CIS-2,6-DIMETHYLMORPHOLINE

The present invention relates to a process for the preparation of cis-2,6-dimethylmorpholine from trans-2,6-dimethylmorpholine by isomerization over a palladium-containing catalyst in the presence of hydrogen.

U.S. Pat. No. 3,083,202 discloses that the proportion of cis-compound in a mixture of cis- and trans-2,6-dimethylmorpholine can be increased by heating this mixture with concentrated or fuming sulfuric acid at from 185° to 220° C. Instances of cis-trans rearrangements carried out over hydrogenation catalysts have also been disclosed (Houben-Weyl, "Methoden der organischen Chemie", Volume 4/2, pages 227-283). For example, cis-1,4-dimethylcyclohexane can be rearranged to trans-1,4-dimethylcyclohexane in the presence of a nickel catalyst at 175° C. [N. D. Zelinsky and E. J. Margolis, Ber. dtsch. chem. Ges. 65 (1932), 1613].

We have found that cis-2,6-dimethylmorpholine of the formula I

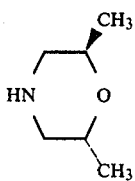

I is obtained in a simple manner if trans-2,6-dimethylmorpholine of the formula II

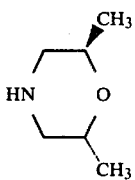

II is converted in the presence of hydrogen and of a palladium-containing catalyst which additionally contains zinc, cadmium or manganese or a mixture of these.

The advantage of the novel process is that cis-2,6-dimethylmorpholine is obtained substantially free from by-products and waste products. By contrast, the conventional isomerization by means of sulfuric acid produces, on subsequent neutralization of the mixture with alkalis and liberation of the 2,6-dimethylmorpholine base, alkali metal sulfates which are undesired by-products, must be discharged into rivers, and pollute the environment.

Cis/trans rearrangements of appropriately substituted morpholine rings in the presence of a hydrogenation catalyst have not previously been disclosed.

The conversion according to the invention can be carried out continuously or batchwise. As a rule, it is effected at from 120° to 280° C., advantageously from 150° to 250° C., under a pressure of from 1 bar (atmospheric pressure) to 200 bar, advantageously from 1 bar to 50 bar. It may be carried out in the absence of a solvent or in the presence of a solvent which is inert under the reaction conditions.

Examples of suitable solvents are cyclohexane, cyclopentane, methylcyclopentane, hexane, heptane, cyclohexyl methyl ether, di-n-butyl ether, tetrahydrofuran and tert.-butanol.

The catalysts used are palladium catalysts which additionally contain zinc, cadmium or manganese or a mixture of these. Preferably, the catalysts are employed on carriers. Examples of suitable inert carriers are active charcoal, $SiO_2$ and $Al_2O_3$. The addition of a basic metal oxide, for example a rare earth metal oxide, eg. $Pr_2O_3$, $La_2O_3$, $CeO_2$, $Nd_2O_3$, $Gd_2O_3$ or $Sm_2O_3$, proves very advantageous.

The palladium content of the catalyst, based on carrier, is not critical and can be varied within wide limits, but is advantageously from 0.05 to 15% by weight. The content of the additional components of the catalyst (zinc, cadmium or manganese or a mixture of these) is advantageously in each case from 0.01 to 10% by weight, based on carrier. The weight ratio of the additional components of the catalyst to palladium metal can be, for example, from 400:1 to 1:150, preferably from 50:1 to 1:10. The content of rare earth oxides in the catalyst can be, for example, from 0.2 to 20% by weight, based on carrier. The catalyst may be used in the form of, for example, a powder or extrudates.

The catalyst can be prepared in a conventional manner, for example by impregnating the inert carrier with carbonates of the metals and then heating the impregnated material.

The cis-2,6-dimethylmorpholine prepared by the process of the invention is used as an intermediate for the preparation of active ingredients of crop protection agents (cf. German Laid-Open Applications DOS Nos. 2,656,747, 2,752,096 and 2,752,135).

In the Examples which follow, parts are by weight and bear the same relation to parts by volume as that of the liter to the kilogram.

EXAMPLE 1

1,000 parts by volume in a fluidized bed furnace having a total capacity of 1,300 parts by volume are filled with a catalyst consisting of 0.5% by weight of palladium, 0.11% by weight of zinc and 0.1% by weight of cadmium on aluminum oxide. The catalyst is used in the form of a powder, the particle size being from 0.2 to 0.6 mm. After the catalyst has been introduced into the furnace, it is heated to 220° C. and is fluidized by simultaneously introducing 300,000 parts by volume of hydrogen per hour and 100,000 parts by volume of nitrogen per hour. 100 parts of trans-2,6-dimethylmorpholine are passed, per hour, through this fluidized bed of catalyst. The reaction product issuing from the fluidized bed furnace is cooled, giving 100 parts per hour of the conversion product.

Analysis of this product by gas chromatography shows that it contains 86% of cis-2,6-dimethylmorpholine and 14% of trans-2,6-dimethylmorpholine.

Fractionation of 1,200 parts of the crude product, using a packed column with 60 theoretical plates, gives 846 parts of pure cis-2,6-dimethylmorpholine, boiling point 80°-81° C./100 mm Hg. This corresponds to a yield of 70.5% (without allowing for the trans-2,6-dimethylmorpholine which can be recycled to the fluidized bed). In addition, 306 parts of a fraction consisting predominantly of trans-2,6-dimethylmorpholine, boiling point 87°-90° C./100 mm Hg, are obtained. 48 parts of higher-boiling products (constituting the distillation residue) are obtained. The selectivity of the conversion is 96%.

EXAMPLE 2

A stirred autoclave having a capacity of 300 parts by volume is charged with a mixture of 150 parts of trans-2,6-dimethylmorpholine and 3 parts of a catalyst which consists of 10% by weight of palladium, 5% by weight of praseodymium oxide and 1% by weight of manganese on aluminum oxide. The autoclave is sealed and hydrogen is then forced in until the pressure reaches 15 bar. The charge is then heated for 12 hours at 230° C. under autogenous pressure (about 30 bar). The material discharged from the reactor is filtered and the filtrate is purified by distillation (without fractionation). The distillate, amounting to 138 parts, consists of 73% of cis-2,6-dimethylmorpholine and 27% of trans-2,6-dimethylmorpholine. 12 parts of distillation residue remain. From these data, the selectivity is calculated to be 92%.

We claim:

1. A process for the preparation of cis-2,6-dimethylmorpholine by isomerizing trans-2,6-dimethylmorpholine, wherein trans-2,6-dimethylmorpholine is converted, in the presence of hydrogen and of a catalyst containing palladium as well as zinc, cadmium or manganese or a mixture of these, at from 120° to 280° C., especially from 150° to 250° C. under a pressure of from 1 to 200 bar.

2. A process as claimed in claim 1, wherein the catalyst used additionally contains from 0.2 to 20% by weight of a rare earth metal oxide or of a mixture of such oxides.

* * * * *